US012589000B2

(12) United States Patent
Fang et al.

(10) Patent No.: US 12,589,000 B2
(45) Date of Patent: Mar. 31, 2026

(54) MOLDABLE ORTHOPEDIC COMPOSITION WITH ANTI-WASHOUT PROPERTY

(71) Applicant: National Taipei University of Technology, Taipei (TW)

(72) Inventors: Hsu-Wei Fang, Taipei City (TW); Hsiao-Hung Chiang, Taipei City (TW); Chen-Ying Su, Taipei City (TW)

(73) Assignee: NATIONAL TAIPEI UNIVERSITY OF TECHNOLOGY, Taipei (TW)

( * ) Notice: Subject to any disclaimer, the term of this patent is extended or adjusted under 35 U.S.C. 154(b) by 854 days.

(21) Appl. No.: 17/945,618

(22) Filed: Sep. 15, 2022

(65) Prior Publication Data

US 2023/0355394 A1      Nov. 9, 2023

(30) Foreign Application Priority Data

May 9, 2022    (TW) ................................. 111117380

(51) Int. Cl.
| | |
|---|---|
| A61F 2/28 | (2006.01) |
| A61F 5/01 | (2006.01) |
| A61L 27/12 | (2006.01) |
| A61L 31/12 | (2006.01) |

(52) U.S. Cl.
CPC .................. *A61F 2/28* (2013.01); *A61F 5/01* (2013.01); *A61L 27/12* (2013.01); *A61L 31/123* (2013.01)

(58) Field of Classification Search
None
See application file for complete search history.

(56) References Cited

U.S. PATENT DOCUMENTS

| | | | | |
|---|---|---|---|---|
| 2008/0031917 A1* | 2/2008 | Miller | .................. | A61L 27/446 |
| | | | | 424/549 |
| 2012/0130435 A1* | 5/2012 | Hart | .................. | A61L 24/0015 |
| | | | | 606/301 |

FOREIGN PATENT DOCUMENTS

| | | | | |
|---|---|---|---|---|
| WO | WO-2013096797 A2 * | 6/2013 | .............. | A61P 19/08 |

OTHER PUBLICATIONS

Chiang et al. (Appl. Sci. Sep. 2, 2021; (11); 8136: 10 pages). (Year: 2021).*

* cited by examiner

*Primary Examiner* — Ernst V Arnold

(74) *Attorney, Agent, or Firm* — Birch, Stewart, Kolasch & Birch, LLP

(57) ABSTRACT

Provided is an orthopedic composition, including: a powder composition including calcium sulfate hemihydrate, β-tri-calcium phosphate and hydroxypropyl methylcellulose; and a solvent including glycerol and water. The orthopedic composition exhibits improved washout resistance. A method of manufacturing the orthopedic composition and a bone graft set including the orthopedic composition are further provided.

8 Claims, 2 Drawing Sheets

MOLDABLE ORTHOPEDIC COMPOSITION WITH ANTI-WASHOUT PROPERTY

BACKGROUND OF THE INVENTION

Field of the Invention

The present disclosure relates to a bone graft material and, more particularly, to a moldable orthopedic composition with improved washout resistance.

Description of the Prior Art

Calcium sulfate has long been used in bone healing because of its good osteoconduction and biocompatibility. Calcium sulfate is suitable for use in making fillers for filling cavities. Calcium sulfate is conducive to restoring bone shapes and outlines, stopping soft tissue invasions, and enhancing vascular infiltration, and its degradation speed suits the speed of bone regeneration. When calcium sulfate is placed at bone defects, it releases calcium ions. Once their concentration gradient reaches a specific level, the calcium ions will bind to phosphate ions normally existing in the human body to cause precipitation of calcium phosphate. During the process of bone repair, precipitation of phosphate groups brings secondary osteoinduction, thereby enabling osteoblast attachment. When degradation of the calcium sulfate starts, the pH of peripheral tissue indicates mild acidity thereof, causing demineralization of peripheral bone tissue. The phenomenon of demineralization is accompanied by the release of a growth factor to cause osteoinduction, promoting differentiation of surrounding stem cells; cell growth is followed by mineralization, resulting in bone regeneration [1].

Calcium sulfate falls under three categories according to the amount of crystalline hydrate, namely calcium sulfate dihydrate $(CaSO_4 \cdot 2H_2O)$, calcium sulfate hemihydrate $(CaSO_4 \cdot 0.5H_2O)$, and calcium sulfate dehydrate. Calcium sulfate dihydrate is also known as gypsum. Calcium sulfate hemihydrate is also known as plaster. Both calcium sulfate dihydrate and calcium sulfate hemihydrate are applicable to a bone graft material. However, if neither special treatment is performed on calcium sulfate nor additive is added thereto, calcium sulfate will be rapidly degraded in the human body and thus cannot provide initial support capability at the defects and cellular attachment. Therefore, plenty studies focus on developing calcium sulfate composite materials, so that calcium sulfate becomes a much better bone graft material. (1) α-tricalcium phosphate (α-TCP) is added to calcium sulfate: calcium sulfate and α-TCP are mixed to take on a stable structure, so that the duration of degradation lasts 1 to 2 years, wherein holes are formed in the calcium sulfate in the mixture as a result of degradation thereof, thereby facilitating bone ingrowth [2-3]. (2) Hydroxylapatite (HAp) is added to calcium sulfate: Hydroxylapatite (HAp) is a major inorganic constituent of human bone and exhibits good biocompatibility, and it has a calcium-phosphorus ratio of 1.67; thus, it is similar to bone in terms of mineral composition and can bond with bone to become part of the bone, albeit with overly low mechanical strength; thus, when Hydroxylapatite (HAp) and calcium sulfate together form a composite material, an increase in the proportion of calcium sulfate in the composite material causes an increase in the mechanical strength of implants [4]; degradation of calcium sulfate causes formation of holes, thereby facilitating bone ingrowth. (3) Sodium alginate, chitosan, methylcellulose or hyaluronic acid is added to calcium sulfate hemihydrate: owing to the introduction of these additives, calcium sulfate hemihydrate has a longer duration of degradation and satisfactory operation properties, despite its reduced mechanical strength (for example, upon the introduction of sodium alginate or chitosan); given an appropriate proportion, for example, methylcellulose proportion greater than 7.5% or hyaluronic acid proportion greater than 5%, pressure resistance strength increases, rendering the material more stable [5-6]. (4) Decellularized bone matrix is added to calcium sulfate hemihydrate: decellularized bone matrix not only enables biocompatibility and osteoconduction but also provides osteoinduction and growth factor [7], despite its disadvantages of poor mechanical strength, infection risk and acquisition source; thus, calcium sulfate hemihydrate-containing composite bone materials can provide initial mechanical strength and early-stage vascular invasion [8].

Among commercially-available bone graft materials, calcium sulfate products are mostly injection-based. Calcium phosphate comes in the form of ingot-shaped, sheet-shaped, cylindrical shape, and injection type. Some bioglass (calcium silicate) and polymeric materials (polylactic acid, polyglycolic acid) are incorporated into bone graft materials. Before injection-based or hydrate materials are put into use, the powder and the liquid have to be mixed such that the mixture becomes thick enough to be introduced into an injection container or becomes as thick as clay in order to correspond in shape to a lesion, so as to be moldable to take on a desirable shape required for filling.

The mixing process is confronted with two issues as follows [9]:

During the mixing process, the powder and water are not mixed evenly, and in consequence material properties alter, leading to changes in predetermined curing duration, injection properties, and mechanical properties. Existing methods of mixing commercially-available products are different. For instance, product A requires mixing powder and water evenly within one minute and then allowing the mixture to stand still for three minutes before being filled into a lesion. By contrast, product B requires immersing powder in water for three minutes and then mixing them for one minute before filling the mixture into the lesion. Commercially-available products are not governed by a unified mixing rule, thereby causing confusions to surgeons.

Before being cured, a material has to be implanted into a patient's body by a surgeon. If the curing duration is too short, the implanted material will lose its injection properties. If the curing duration is too long, the surgery will take longer and thus pose a greater risk to the patient.

Therefore, a pre-mixed preparation is provided. The pre-mixed preparation is designed to not only spare surgeons the hassle of mixing powder and water after unwrapping the package but also enable the surgeons to perform the filling process immediately to thereby enhance the ease of use and reduce the risks otherwise posed to the patients.

Among bone graft materials commercially-available in Taiwan, only GeneX® Bone Graft Substitute provides a pre-mixed moldable bone graft material. Nonetheless, clinical findings show that this product predisposes patients to inflammatory reactions and even formation of inflammatory cysts at the site of implantation [10-11]. The existing explanation is that degradation of calcium sulfate in GeneX® Bone Graft Substitute causes a decrease in the pH level at the site of implantation and resultant material liquefaction, leading to fragmentation and the ensuing inflammatory reactions [11].

Therefore, it is important to provide a moldable bone graft material with improved washout resistance which lasts long and works well.

SUMMARY OF THE INVENTION

In view of the aforesaid drawbacks of the prior art, it is important to study and improve orthopedic compositions. Thus, it is an objective of the present disclosure to provide a moldable orthopedic composition with improved washout resistance and its manufacturing method. Another embodiment of the present disclosure provides a moldable orthopedic composition with improved washout resistance.

In order to achieve the above and other objectives, the present disclosure provides a moldable orthopedic composition comprising: a powder composition comprising calcium sulfate hemihydrate ($CaSO_4 \cdot 0.5H_2O$), β-tricalcium phosphate (β-TCP) and hydroxypropyl methylcellulose (HPMC), and a solvent comprising glycerol and water.

Preferably, the ratio of the calcium sulfate hemihydrate to the β-tricalcium phosphate (β-TCP) is approximately 1:1 (gram/gram).

Preferably, the hydroxypropyl methylcellulose has a percent by weight of 1~6%.

Preferably, the hydroxypropyl methylcellulose has a percent by weight of approximately 1~4%.

Preferably, the glycerol has a percent by volume of approximately 70~99%.

Preferably, the glycerol has a percent by volume of approximately 85%.

Another objective of the present disclosure is to provide a bone graft set which comprises the moldable orthopedic composition stored in a standalone container.

In order to achieve the above and other objectives, the present disclosure further provides a medical use of a moldable orthopedic composition for use in treating bone defects.

BRIEF DESCRIPTION OF THE DRAWINGS

Embodiments of the present disclosure and their advantages are illustrated by accompanying drawings and described below.

DETAILED DESCRIPTION OF THE EMBODIMENTS

Figure 1:
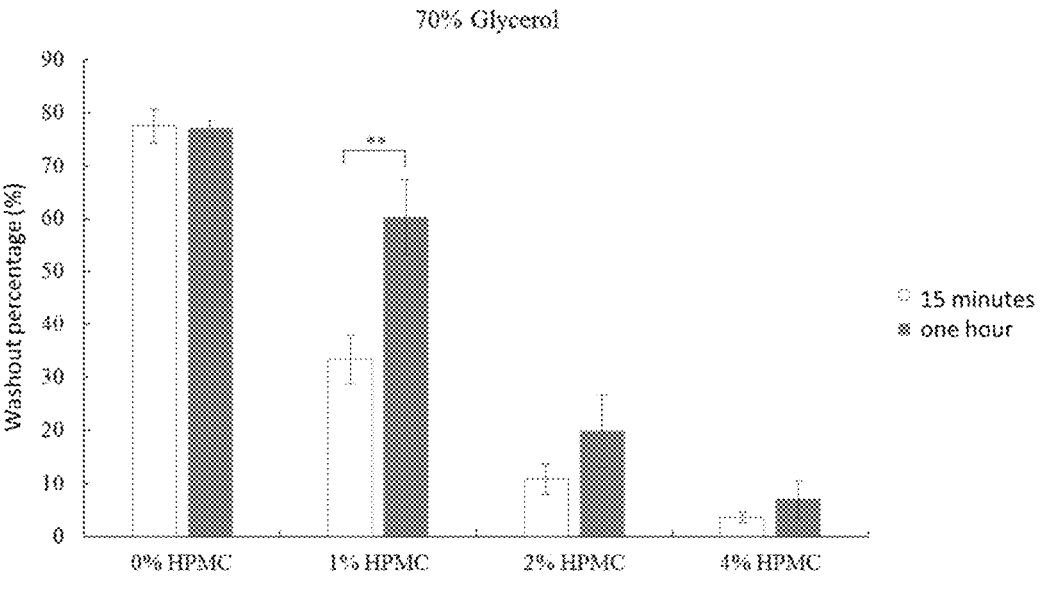
FIG. 1 shows orthopedic compositions comprising 70% glycerol but comprising hydroxypropyl methylcellulose (HPMC) of different proportions and shows the washout percentage of the orthopedic compositions being immersed in a simulation body fluid for 15 minutes or one hour. The experiment of FIG. 1 uses t-test, the same formula for **$P<0.01$, and immersion duration of 15 minutes and one hour to evaluate the difference therebetween.

The present disclosure is illustrated by preferred embodiments, depicted by drawings, and described below. Experimental data disclosed in the embodiments is intended to facilitate interpretation of technical features of the present disclosure but is not restrictive of implementable aspects of the present disclosure.

The adverb "approximately" used herein is indicative of errors in material proportions, errors in medicament concentrations, and variations between experimental subjects. Typically, the adverb "approximately" indicates the variety of being greater than or less than 1%, 2%, 3%, 4%, 5%, 6%, 7%, 8%, 9%, 10%, 11%, 12%, 13%, 14%, 15%, 16%, 17%, 18%, 19% or 20%, as appropriate.

The specific aspects of the expression "orthopedic composition" used herein include, but are not limited to, joint implants, vertebral implants, craniomaxillofacial implants, dental implants, ankle implants and traumatic implants (plates and nails).

The expressions "injected," "injection" and "injectability" used herein mean administering such as injecting, infusing, or delivering any composition to the body through transmission by any conveying device.

It is an objective of the present disclosure to provide a moldable orthopedic composition comprising: a powder composition comprising calcium sulfate hemihydrate ($CaSO_4 \cdot 0.5H_2O$), β-tricalcium phosphate (β-TCP) and hydroxypropyl methylcellulose (HPMC), and a solvent comprising glycerol and water.

In a specific embodiment of the present disclosure, the ratio of the calcium sulfate hemihydrate to the β-tricalcium phosphate (β-TCP) is approximately 1:1 (gram/gram).

In a specific embodiment of the present disclosure, the hydroxypropyl methylcellulose has a percent by weight of approximately 1~6%, preferably approximately 1~4%, and most preferably approximately 2~4%, of the powder composition. If the percent by weight of the hydroxypropyl methylcellulose is greater than 6%, the orthopedic composition of the present disclosure will be overly sticky and thus too difficult to manipulate and serve as a moldable orthopedic composition.

In a specific embodiment of the present disclosure, the liquid-to-powder ratio of the powder composition to the solvent is most preferably approximately 0.35 milliliter/gram. In a specific embodiment of the present disclosure, the calcium sulfate hemihydrate has a percent by weight of approximately 47, 47.5, 48, 48.5, 49, 49.5%, preferably approximately 48, 48.5, 49, 49.5%, most preferably approximately 48, 48.5, 49%, of the powder composition. In a specific embodiment of the present disclosure, the β-tricalcium phosphate (β-TCP) has a percent by weight of approximately 47, 47.5, 48, 48.5, 49, 49.5%, preferably approximately 48, 48.5, 49, 49.5%, most preferably approximately 48, 48.5, 49%, of the powder composition. In a specific embodiment of the present disclosure, the hydroxypropyl methylcellulose has a percent by weight of approximately 1, 2, 3, 4, 5, 6%, preferably approximately 1, 2, 3, 4%, most preferably approximately 2, 3, 4%, of the powder composition.

In a specific embodiment of the present disclosure, the glycerol has a percent by volume of approximately 70~99%, preferably approximately 85%, of the solvent. If the percent by volume of the glycerol is less than 70%, the orthopedic composition of the present disclosure will be likely to disintegrate, for example, within one day, and thus cannot effectively take shape.

The orthopedic composition of the present disclosure further includes a dispersing agent for uniformly distributing a powder, suspension stabilizer for maintaining the suspension state of the powder particles, medicament (for example, osteoblastic bone formation/differentiation promotor, neovascularization promotor), nutrient, antimicrobial agent, antibiotic or additive (for example, curing promotor, curing retarder).

Another objective of the present disclosure is to provide a bone graft set comprising the moldable orthopedic composition stored in a standalone container. The injection orifice of a common conventional bone graft syringe has an inner diameter of 3 mm approximately; thus, the fluidity of the orthopedic composition in the course of injection depends on the particle diameters of the calcium sulfate hemihydrate, β-tricalcium phosphate (β-TCP) and hydroxypropyl methylcellulose. To enable the orthopedic composition of the present disclosure to exhibit preferred fluidity and thereby be easy to be squeezed out, the calcium sulfate hemihydrate of the present disclosure preferably has an average particle diameter of 20~40 μm, the β-tricalcium phosphate (β-TCP) of the present disclosure preferably has an average particle diameter of 20~40 μm, and the hydroxypropyl methylcellulose of the present disclosure preferably has an average particle diameter of 100~200 μm.

Yet another objective of the present disclosure is to provide a medical use of the moldable orthopedic composition in treating bone defects.

The present disclosure is illustrated by embodiments and described below. However, the embodiments are not restrictive of the present disclosure. Persons skilled in the art may make slight improvements and modifications in the embodiments without departing from the scope of the present disclosure.

EMBODIMENT

Orthopedic Composition Manufacturing Method

The orthopedic composition is prepared according to the proportions shown in Table 1.

TABLE 1

| Orthopedic composition code | | A | B | C | D | E | F |
|---|---|---|---|---|---|---|---|
| Powder | CaSO$_4$•0.5H$_2$O | 50 | 49.5 | 49 | 48 | 50 | 49.5 |
| (%) | β-TCP | 50 | 49.5 | 49 | 48 | 50 | 49.5 |
| | HPMC | 0 | 1 | 2 | 4 | 0 | 1 |
| Solvent | Glycerol | 70 | 70 | 70 | 70 | 85 | 85 |
| (%) | Water | 30 | 30 | 30 | 30 | 15 | 15 |

TABLE 1-continued

| Orthopedic composition code | | G | H | I | J | K | L |
|---|---|---|---|---|---|---|---|
| Powder | CaSO$_4$•0.5H$_2$O | 49 | 48 | 50 | 49.5 | 49 | 48 |
| (%) | β-TCP | 49 | 48 | 50 | 49.5 | 49 | 48 |
| | HPMC | 2 | 4 | 0 | 1 | 2 | 4 |
| Solvent | Glycerol | 85 | 85 | 99 | 99 | 99 | 99 |
| (%) | Water | 15 | 15 | 1 | 1 | 1 | 1 |

The method of manufacturing the orthopedic composition is carried out according to the percent by weight shown in Table 1 and involves mixing the powder of the calcium sulfate hemihydrate (with an average particle diameter of 20~40 μm), the powder of the β-tricalcium phosphate (β-TCP) (with an average particle diameter of 20~40 μm) and the powder of the hydroxypropyl methylcellulose (with an average particle diameter of 100~200 μm), mixing the glycerol and water according to the percent by volume shown in Table 1, adding the glycerol-water mixture to the powders at room temperature, and blending the mixture and powders with a pharmaceutical spoon to form a moldable orthopedic composition with improved washout resistance.

Washout Experiment Method

The moldable orthopedic composition is placed inside a 304 stainless steel die (with a diameter of 6 millimeters and a height of 3 millimeters) to take on a cylindrical shape and be weighed. Then, the moldable orthopedic composition is immersed centrally in the bottom of a barrel that contains a simulation body fluid. The barrel has a diameter of 20 millimeters and a height of 20 millimeters and is placed in an environment at 37° C. The ratio of the orthopedic composition to the simulation body fluid is specified to be 0.2 gram of bone graft material to 1 milliliter of simulation body fluid. The simulation body fluid is used, because its ionic concentration approximates to that of the human blood plasma [12]. The immersion of the orthopedic composition in the simulation body fluid lasts 15 minutes, one hour or four hours and is followed by the removal of the simulation body fluid and the introduction of 1 milliliter of 99.5% alcohol, and then the orthopedic composition is placed at room temperature for 30 seconds. After that, alcohol is removed, and then both the intact bone graft material proper (a cylinder with a diameter of 6 millimeters) and the disintegrated fragments are placed in an oven operating at 50° C. for three days. Next, the intact bone graft material proper is weighed. The weight of the intact bone graft material proper is subtracted from pre-experiment weight to figure out weight loss. Then, the weight loss is divided by the pre-experiment weight to obtain washout percentage. Therefore, the lower the washout percentage is, the better the washout resistance of the formula is.

Embodiment 1

The results of immersing the orthopedic composition in the simulation body fluid for 15 minutes are shown in Table 2.

TABLE 2

| Orthopedic composition code | A | B | C | D | E | F |
|---|---|---|---|---|---|---|
| Pre-experiment weight (gram) | 0.194 | 0.193 | 0.198 | 0.194 | 0.193 | 0.195 |
| Weight (gram) after its immersion in simulation body fluid for 15 minutes | 0.044 | 0.129 | 0.176 | 0.187 | 0.051 | 0.123 |
| Weight loss = pre-experiment weight − | 0.151 | 0.064 | 0.021 | 0.007 | 0.141 | 0.073 |

TABLE 2-continued

| | | | | | | |
|---|---|---|---|---|---|---|
| weight (gram) after its immersion in liquid | | | | | | |
| Washout percentage = weight loss ÷ pre-experiment weight | 77.52% ± 3.19 | 33.39% ± 4.61 | 10.80% ± 2.85 | 3.55% ± 1.07 | 73.35% ± 2.40 | 37.06% ± 6.75 |

| Orthopedic composition code | G | H | I | J | K | L |
|---|---|---|---|---|---|---|
| Pre-experiment weight (gram) | 0.199 | 0.194 | 0.193 | 0.193 | 0.190 | 0.198 |
| Weight (gram) after its immersion in simulation body fluid for 15 minutes | 0.172 | 0.182 | 0.034 | 0.044 | 0.120 | 0.158 |
| Weight loss = pre-experiment weight − weight (gram) after its immersion in liquid | 0.027 | 0.012 | 0.160 | 0.149 | 0.070 | 0.040 |
| Washout percentage = weight loss ÷ pre-experiment weight | 13.76% ± 7.32 | 6.20% ± 2.77 | 82.62% ± 3.07 | 77.33% ± 4.71 | 36.91% ± 3.38 | 20.25% ± 7.48 |

The results of immersing the orthopedic composition in the simulation body fluid for one hour are shown in Table 3.

TABLE 3

| Orthopedic composition code | A | B | C | D | E | F |
|---|---|---|---|---|---|---|
| Pre-experiment weight (gram) | 0.193 | 0.191 | 0.192 | 0.193 | 0.192 | 0.197 |
| Weight (gram) after its immersion in simulation body fluid for one hour | 0.044 | 0.076 | 0.153 | 0.18 | 0.048 | 0.053 |
| Weight loss = pre-experiment weight − weight (gram) after its immersion in liquid | 0.148 | 0.115 | 0.038 | 0.013 | 0.144 | 0.144 |
| Washout percentage = weight loss ÷ pre-experiment weight | 76.98% ± 1.42 | 60.20% ± 7.19 | 19.80% ± 6.69 | 6.96% ± 3.54 | 74.80% ± 2.43 | 73.14% ± 3.91 |

| Orthopedic composition code | G | H | I | J | K | L |
|---|---|---|---|---|---|---|
| Pre-experiment weight (gram) | 0.193 | 0.196 | 0.200 | 0.198 | 0.195 | 0.192 |
| Weight (gram) after its immersion in simulation body fluid for one hour | 0.125 | 0.165 | 0.044 | 0.044 | 0.116 | 0.157 |
| Weight loss = pre-experiment weight − weight (gram) after its immersion in liquid | 0.068 | 0.031 | 0.156 | 0.154 | 0.079 | 0.036 |
| Washout percentage = weight loss ÷ pre-experiment weight | 35.16% ± 1.26 | 15.81% ± 1.32 | 78.24% ± 2.51 | 77.72% ± 3.81 | 40.34% ± 3.18 | 18.55% ± 6.67 |

Figure 2:
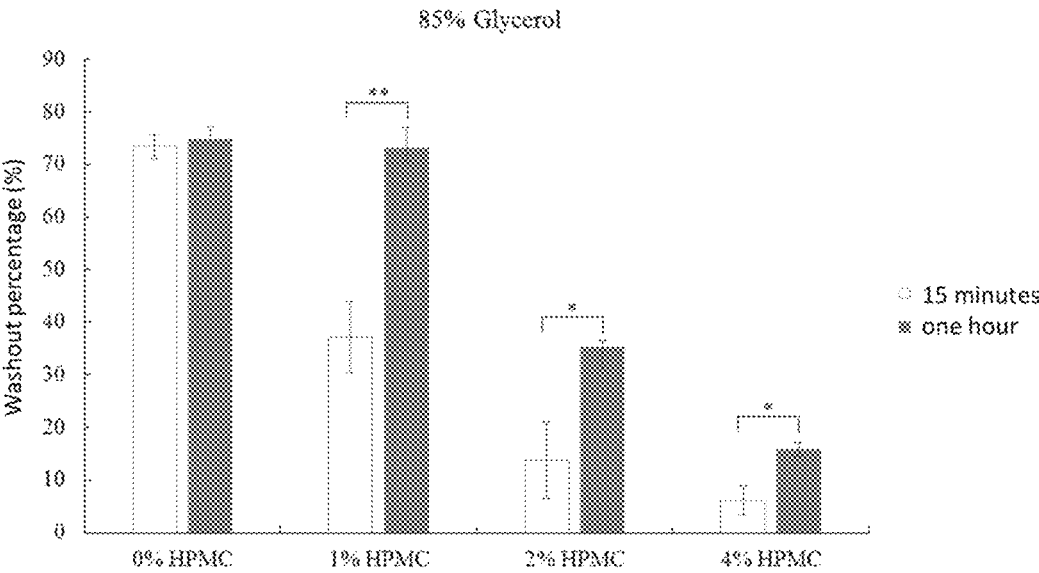
FIG. 2 shows orthopedic compositions comprising 85% glycerol but comprising hydroxypropyl methylcellulose (HPMC) of different proportions and shows the washout percentage of the orthopedic compositions being immersed in a simulation body fluid for 15 minutes or one hour. The experiment of FIG. 2 uses t-test, the same formula for *$P<0.05$ or **$P<0.01$, and immersion duration of 15 minutes and one hour to evaluate the difference therebetween.
Figure 3:
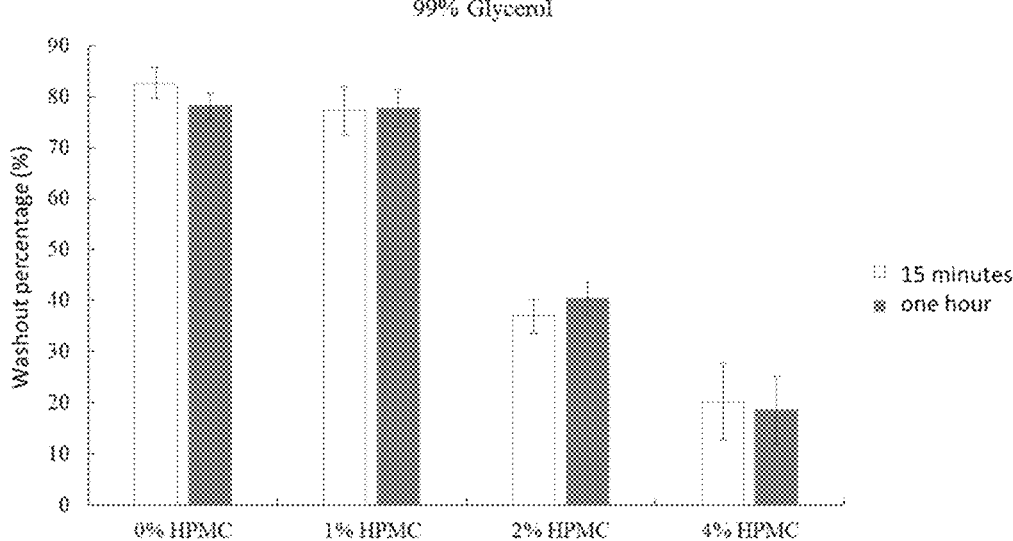
FIG. 3 shows bone graft materials comprising 99% glycerol but comprising hydroxypropyl methylcellulose (HPMC) of different proportions and shows the washout percentage of the bone graft materials being immersed in a simulation body fluid for 15 minutes or one hour. The experiment of FIG. 3 uses t-test and immersion duration of 15 minutes and one hour, only to find no statistical difference therebetween.

The data in Table 1 and Table 2 indicates that the introduction of the hydroxypropyl methylcellulose (HPMC) into the orthopedic composition effectively decreases the percentage of the orthopedic composition. Thus, the higher the percentage of the hydroxypropyl methylcellulose is, the greater the washout resistance of the orthopedic composition is. As shown in FIGS. 1, 2, 3, the hydroxypropyl methylcellulose markedly augments long-term washout resistance of the orthopedic composition, especially in the presence of 85% glycerol.

Embodiment 2

The results of immersing the moldable orthopedic composition in the simulation body fluid for four hours are shown in Table 4.

TABLE 4

| Orthopedic composition code | A | B | C | D | E | F |
|---|---|---|---|---|---|---|
| Pre-experiment weight (gram) | 0.188 | 0.195 | 0.188 | 0.190 | 0.191 | 0.192 |
| Weight (gram) after its immersion in simulation body fluid for four hours | 0.036 | 0.038 | 0.107 | 0.132 | 0.040 | 0.042 |
| Weight loss = pre-experiment weight − weight (gram) after its immersion in liquid | 0.152 | 0.157469 | 0.081 | 0.057 | 0.151 | 0.150 |
| Washout percentage = weight loss ÷ pre-experiment weight | 81.01% ± 1.88 | 80.62% ± 3.85 | 42.99% ± 2.81 | 30.18% ± 4.94 | 79.03% ± 0.13 | 77.91% ± 1.55 |

| Orthopedic composition code | G | H | I | J | K | L |
|---|---|---|---|---|---|---|
| Pre-experiment weight (gram) | 0.198 | 0.197 | 0.192 | 0.186 | 0.187 | 0.191 |
| Weight (gram) after its immersion in simulation body fluid for one hour | 0.086 | 0.119 | 0.009 | 0.026 | 0.068 | 0.111 |
| Weight loss = pre-experiment weight − weight (gram) after its immersion in liquid | 0.111 | 0.078 | 0.182 | 0.160 | 0.119 | 0.080 |
| Washout percentage = weight loss ÷ pre-experiment weight | 56.21% ± 2.45 | 39.5% ± 2.56 | 95.10% ± 0.87 | 85.87% ± 2.50 | 63.49% ± 6.03 | 41.82% ± 6.22 |

As shown in Table 4, even though the duration of washout lasts four hours, the hydroxypropyl methylcellulose enhances the washout resistance of the orthopedic composition effectively, especially in the presence of a low proportion of glycerol.

Embodiment 3

The numbers of days of preservation of the orthopedic compositions with different constituents are shown in Table 5.

TABLE 5

| Powder (%) | CaSO$_4$•0.5H$_2$O | 50 | 50 | 50 | 50 | 50 |
|---|---|---|---|---|---|---|
| | β-TCP | 50 | 50 | 50 | 50 | 50 |
| | HPMC | 0 | 0 | 0 | 0 | 0 |
| Liquid (%) | Glycerol | 100 | 70 | 50 | 30 | 0 |
| | Water | 0 | 30 | 50 | 70 | 100 |
| Number of days of preservation | | >21 days | >21 days | <1 day | <1 day | cannot be mixed and cured |
| Moldable at the end of preservation? | | Yes | yes | no | no | not executable |

As shown in Table 5, when the proportion of glycerol is less than 70%, for example, equal to 50% or 30%, preservation of the orthopedic composition lasts a maximum of 1 day, as the orthopedic composition disintegrates within 1 day and thus is unable to take shape. When the proportion of glycerol is greater than 70%, the orthopedic composition is not only moldable but can also be preserved at normal temperature for at least 21 days.

The effect of hydroxypropyl methylcellulose of different concentrations on moldability of orthopedic composition is illustrated by Table 6.

TABLE 6

| Powder (%) | CaSO$_4$•0.5H$_2$O | 49 | 48 | 47 |
|---|---|---|---|---|
| | β-TCP | 49 | 48 | 47 |
| | HPMC | 2 | 4 | 6 |
| Liquid (%) | Glycerol | 70 | 70 | 70 |
| | Water | 30 | 30 | 30 |
| Operation properties | | like styrofoam, moldable | like clay, moldable | like chewing gum, not moldable |

As shown in Table 6, the viscosity of the orthopedic composition increases with the weight percentage of the hydroxypropyl methylcellulose, leading to deterioration of operability. When the concentration of the hydroxypropyl methylcellulose reaches 6%, the orthopedic composition will be as sticky as chewing gum and thus not moldable.

Embodiment 4

The results of comparison of the orthopedic composition of the present disclosure and a commercially-available orthopedic composition are shown in Table 7.

TABLE 7

| Substance tested | Pre-experiment weight (gram) | Weight (gram) after its immersion in water of pH 7.4 for 15 minutes | Weight loss = pre-experiment weight – weight (gram) after its immersion in liquid | Washout percentage = weight loss ÷ pre-experiment weight |
|---|---|---|---|---|
| Orthopedic composition (CaSO$_4$•0.5H$_2$O 48%, β-TCP 48%, HPMC 4%, glycerol 70%, water 30%) of the present disclosure | 5.4 | 4.7 | 0.7 | 12.96% |
| GeneX ® Bone Graft Substitute | 8.8 | 7.5 | 1.3 | 14.77% |

As shown in Table 7, the orthopedic composition of the present disclosure exhibits slightly greater washout resistance than commercially-available GeneX® Bone Graft Substitute. This indicates that the orthopedic composition of the present disclosure has satisfactory washout resistance and moldability.

Calcium sulfate is widely applicable to bone graft materials and has advantages as follows: satisfactory biocompatibility, not toxic, biosorption, and excellent osteoconduction. However, after being implanted in the human body, calcium sulfate is likely to be washed out by blood and thus cannot stay at a point to be filled, thereby failing to perform repair. Therefore, a moldable orthopedic composition with improved washout resistance according to the present disclosure has advantages as follows: the moldable orthopedic composition essentially comprises calcium sulfate and calcium phosphate composition (tetracalcium phosphate and dicalcium phosphate), which are supplemented with citric acid and hydroxypropyl methylcellulose to achieve an effective washout resistance effect and thereby attain excellent restoration capability.

REFERENCE

[1] Urban, R. M., Turner, T. M., Hal, D. J., Inoue, N., Gitelis, S. Increased bone formation using calcium sulfate-calcium phosphate composite graft. Clinical Orthopaedics and Related Research. 2007;459:110-117.

[2] Nilsson, M., Fernandez, E., Sarda, S., Lidgren, L., Planell, J. A. Microstructure analysis of novel resorbable calcium phosphate/sulphate bone cements. Bioceramics. 2002;14:365-368.

[3] Bohner, M. New hydraulic cements based on α-tricalcium phosphate-calcium sulfate dehydrate mixtures. Biomaterials. 2004;25:741-749.

[4] Nilsson, M., Fernandez, E., Sarda, S., Lidgren, L., Planell, J. A. Biodegradation and biocompatibility of a calcium sulfate-hydroxyapatite bone substitute. The Bone & Joint Journal. 2004;86:120-125.

[5] Ikenaga, M., Hardouin, P., Lemaitre, J., Andrianjatovo, H., Flautre, B. Biomechanical characterization of a biodegradable calcium phosphate hydraulic cement: A comparison with porous biphasic calcium phosphate ceramics. Journal of Biomedical Materials Research. 1998;40:139-144.

[6] d'Ayala, G. G., Rosa, A., Laurienzo, P., Malinconico, M. Development of a new calcium sulphate-based composie using alginate and chemically modified chitosan for bone regeneration. Journal of Biomedical Materials Research Part A. 2007;81:811-820.

[7] Rougraff B. T., Kling, T. J. Treatment of activie unicameral bone cysts with percutaneous injection of demineralized bone matrix and autogenous bone marrow. The Journal of Bone Joint Surgery. 2002;84:921-929.

[8] Erdemli, O., Captug, O., Bilgili, H., Orhan, D., Tezcaner, A., Keskin, D. In vitro and in vivo evaluation of the effects of demineralized bone matrix or calcium sulfate addition to polycaprolactone-bioglass composites. Journal of Materials Science: Materials in Medicine. 2010;21:295-308.

[9] Carey, L. E., Xu, H. H., Simon, C. G., Takagi, S., Chow, L. C. Premixed rapid-setting calcium phosphate composites for bone repair. Biomaterials. 2005;26(24):5002-5014.

[10] Friesenbichler, J., Maurer-Ertl, W., Sadoghi, P., Pirker-Fruehauf, U., Bodo, K., Leithner, A. Adverse reactions of artificial bone graft substitutes: lessons learned from using tricalcium phosphate geneX®. Clinical Orthopaedics and Related Research. 2014;472:976-982.

[11] Friesenbichler, J., Maurer-Ertl, W., Sadoghi, P., Pirker-Fruehauf, U., Bodo, K.; Leithner, A. Adverse reactions of artificial bone graft substitutes: lessons learned from using tricalcium phosphate geneX®. Clinical Orthopaedics and Related Research. 2014;472:976-982.

[12] Kokubo, T.; Takadama, H. How useful is SBF in predicting in vivo bone bioactivity? Biomaterials. 2006;27:2907-2915.

What is claimed is:

1. A premixed moldable orthopedic composition, comprising:
   (a) a powder component comprising calcium sulfate hemihydrate, β-tricalcium phosphate (β-TCP), and hydroxypropyl methylcellulose; and
   (b) a liquid component comprising glycerol and water;
   wherein the glycerol is present in an amount of about 70% to about 99% by volume of the liquid component.

2. The premixed moldable orthopedic composition of claim 1, wherein the weight ratio of the calcium sulfate hemihydrate to the β-tricalcium phosphate (β-TCP) is approximately 1:1.

3. The premixed moldable orthopedic composition of claim 1, wherein the hydroxypropyl methylcellulose is present in an amount of 1% to 6% by weight of the powder component.

4. The premixed moldable orthopedic composition of claim 1, wherein the hydroxypropyl methylcellulose is present in an amount of about 1% to about 4% by weight of the powder component.

5. The premixed moldable orthopedic composition of claim 1, wherein the glycerol is present in an amount of about 85% by volume of the liquid component.

6. The premixed moldable orthopedic composition of claim 1, wherein a liquid-to-powder ratio of the liquid component to the powder component is about 0.35 milliliter/gram.

7. A bone graft set, comprising the premixed moldable orthopedic composition of claim 1, wherein the moldable orthopedic composition is contained in a standalone container.

8. A method of treating a bone defect in a subject, comprising:

administering to the bone defect site an effective amount of the premixed moldable orthopedic composition of claim 1.

\* \* \* \* \*